United States Patent
Lu et al.

(10) Patent No.: US 10,758,486 B2
(45) Date of Patent: Sep. 1, 2020

(54) ENGINEERED EXOSOMES FOR THE DELIVERY OF BIOACTIVE CARGO USING TRANSMEMBRANE VSV-G

(71) Applicant: Santa Clara University, Santa Clara, CA (US)

(72) Inventors: Biao Lu, San Francisco, CA (US); Conary Meyer, Santa Clara, CA (US); Joseph Losacco, Lake Forest, IL (US); Zachary Stickney, Mercer Island, WA (US)

(73) Assignee: Santa Clara University, Santa Clara, CA (US)

( * ) Notice: Subject to any disclaimer, the term of this patent is extended or adjusted under 35 U.S.C. 154(b) by 138 days.

(21) Appl. No.: 16/033,383

(22) Filed: Jul. 12, 2018

(65) Prior Publication Data

US 2019/0015333 A1 Jan. 17, 2019

Related U.S. Application Data

(63) Continuation-in-part of application No. 15/648,215, filed on Jul. 12, 2017.

(60) Provisional application No. 62/531,478, filed on Jul. 12, 2017.

(51) Int. Cl.
  *A61K 9/12* (2006.01)
  *A61K 47/42* (2017.01)
  *A61K 47/69* (2017.01)
  *A61K 47/62* (2017.01)
  *A61K 9/127* (2006.01)

(52) U.S. Cl.
  CPC .......... *A61K 9/1277* (2013.01); *A61K 9/1275* (2013.01); *A61K 47/42* (2013.01); *A61K 47/62* (2017.08); *A61K 47/6901* (2017.08)

(58) Field of Classification Search
  None
  See application file for complete search history.

(56) References Cited

U.S. PATENT DOCUMENTS 8,697,439 B2  4/2014  Mangeot

FOREIGN PATENT DOCUMENTS

WO  WO2017054086  4/2017

OTHER PUBLICATIONS

Meyer et al., "Pseudotyping exosomes for enhanced protein delivery in mammalian cells", International Journal of Nanomedicine, Apr. 18, 2017, vol. 12, pp. 3153-3170.*
Stickney et al. Development of exosome surface display technology in living human cells. Biochem Biophys Res Commun. 2016;472(1):53-59.
Afshari et al. A cooled CCD camera-based protocol provides an effective solution for in vitro monitoring of luciferase. Biochem Biophys Res Commun. 2015;458(3):543-548.

* cited by examiner

*Primary Examiner* — Suzanne M Noakes
(74) *Attorney, Agent, or Firm* — Lumen Patent Firm

(57) ABSTRACT

Vesicular stomatitis virus glycoprotein (VSVG) can both load protein cargo onto exosomes and increase their delivery ability via a pseudotyping mechanism. By fusing a set of fluorescent and luminescent reporters with VSVG, we show the successful targeting and incorporation of VSVG fusions into exosomes by gene transfection and fluorescence tracking. VSVG pseudotyping of exosomes does not affect the size or distributions of the exosomes, and both the full-length VSVG and the VSVG without the ectodomain integrate into the exosomal membrane, suggesting that the ectodomain is not required for protein loading. Finally, exosomes pseudotyped with full-length VSVG are internalized by multiple-recipient cell types to a greater degree compared to exosomes loaded with VSVG without the ectodomain, confirming a role of the ectodomain in cell tropism. This invention provides a new genetically encoded pseudotyping platform to load and enhance the intracellular delivery of therapeutic proteins via exosome-based vehicles to target cells.

6 Claims, 20 Drawing Sheets

VSVG construct

N— SP | fVSVG | RFP —C
SP | fVSVG | GFP
SP | RFP | mVSVG
SP | fVSVG | Gluc
SP | Gluc | mVSVG Outside — Inside cell/exosome

FIG. 1B

Expression and localization of VSVG
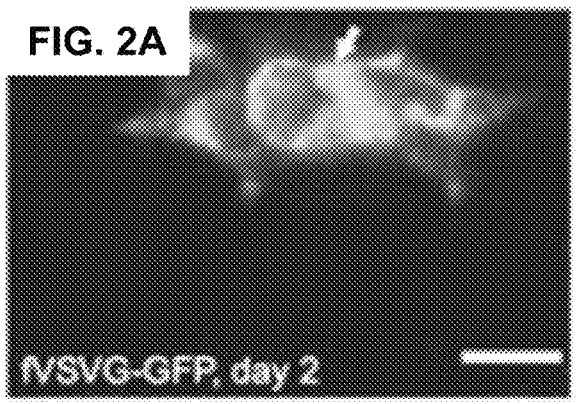
FIG. 2A fVSVG-GFP, day 2
FIG. 2B fVSVG-GFP + phase, day 2
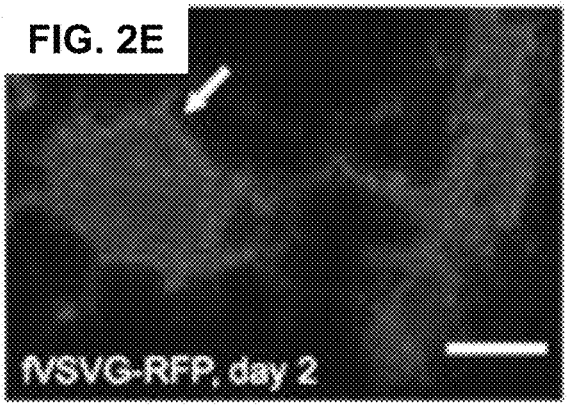
FIG. 2E fVSVG-RFP, day 2
FIG. 2F fVSVG-RFP + phase, day 2
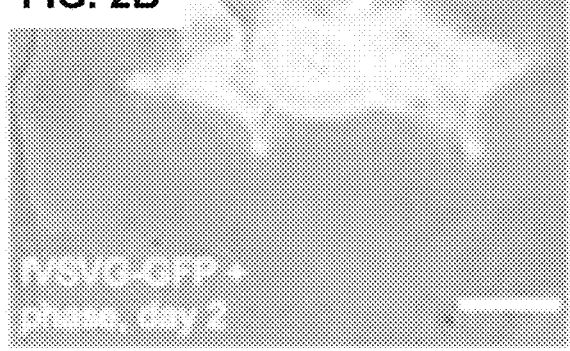
FIG. 2C fVSVG-GFP, day 3
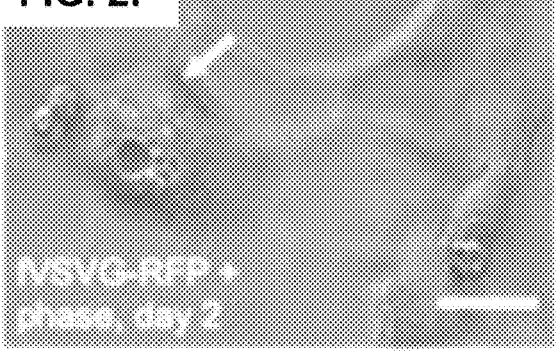
FIG. 2G fVSVG-RFP, day 3
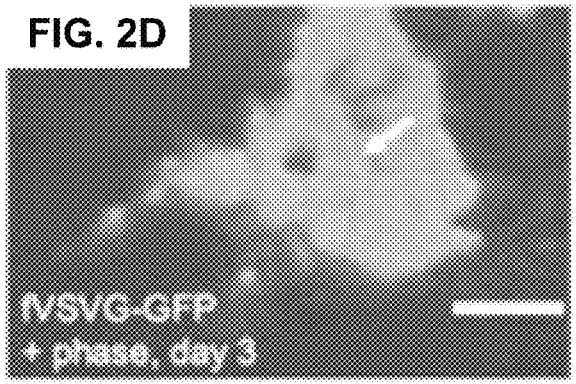
FIG. 2D fVSVG-GFP + phase, day 3
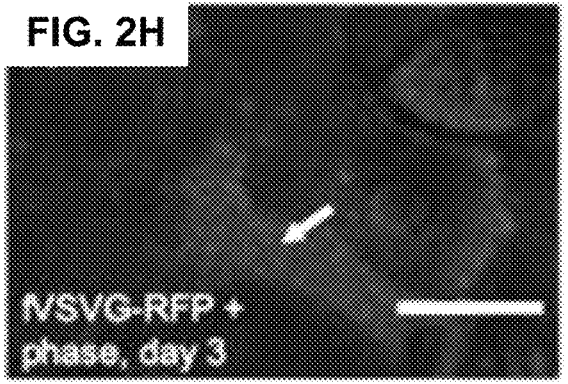
FIG. 2H fVSVG-RFP + phase, day 3

Colocalization of VSVG and Rab5A/CD63 tsVSVG-RFP tsVSVG-RFP

Rab5A-GFP

CD63-GFP

Overlay

Overlay

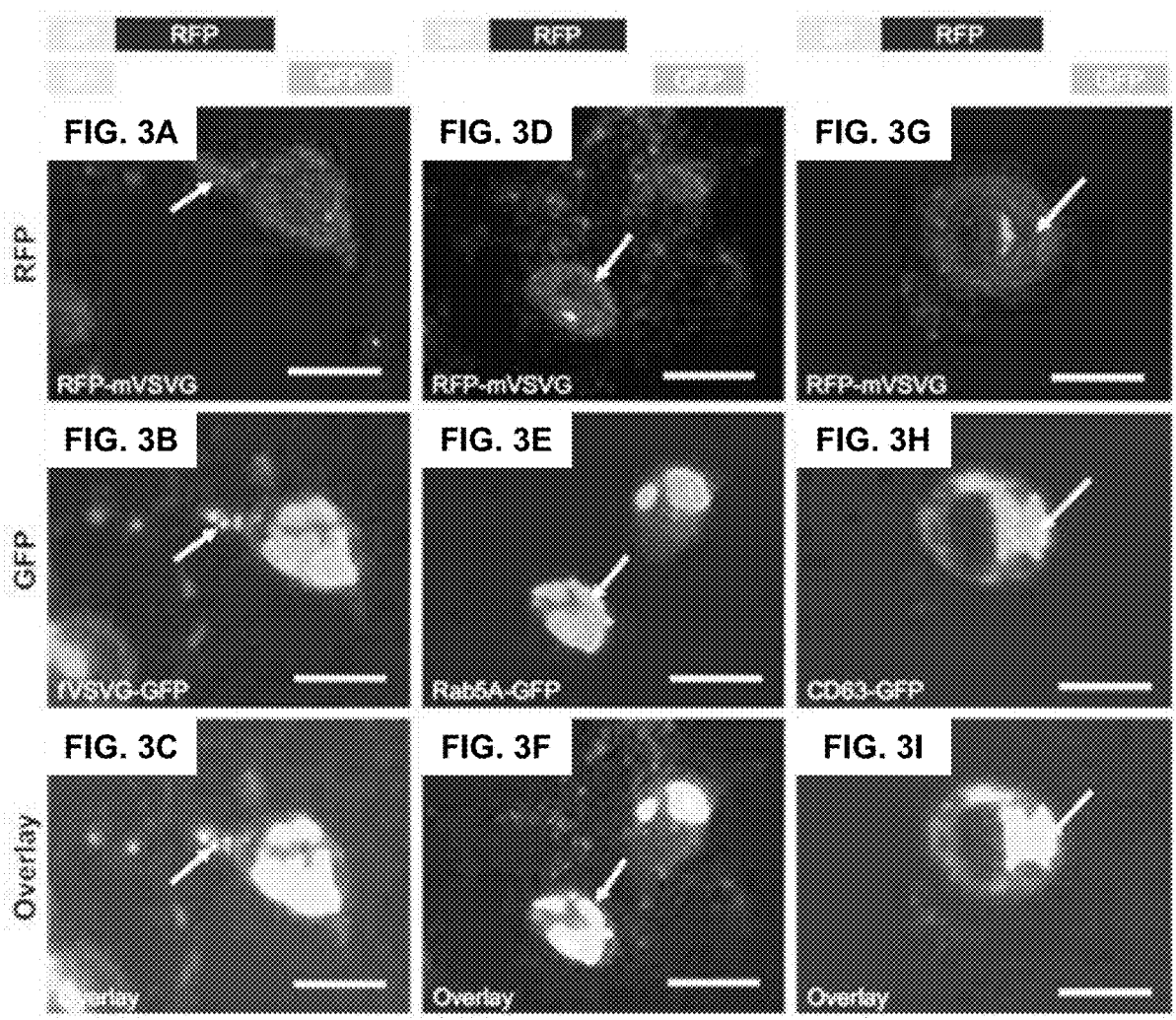

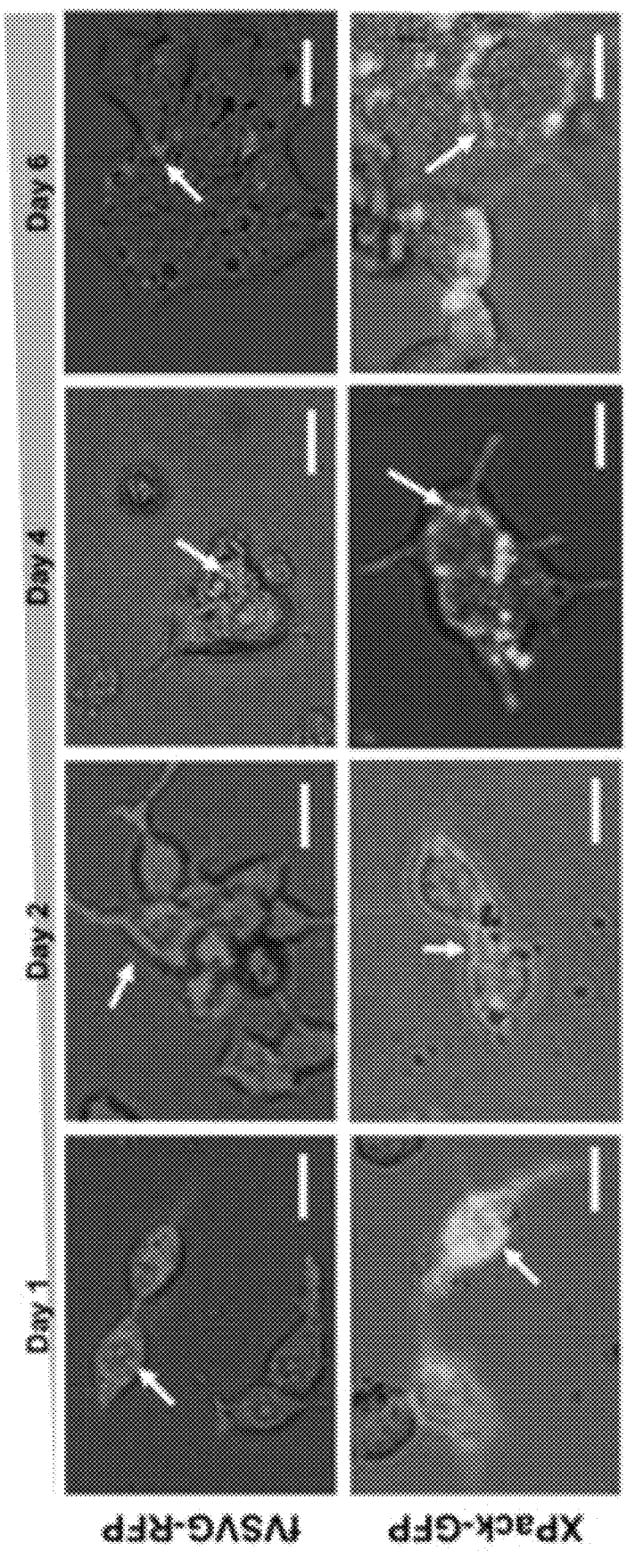
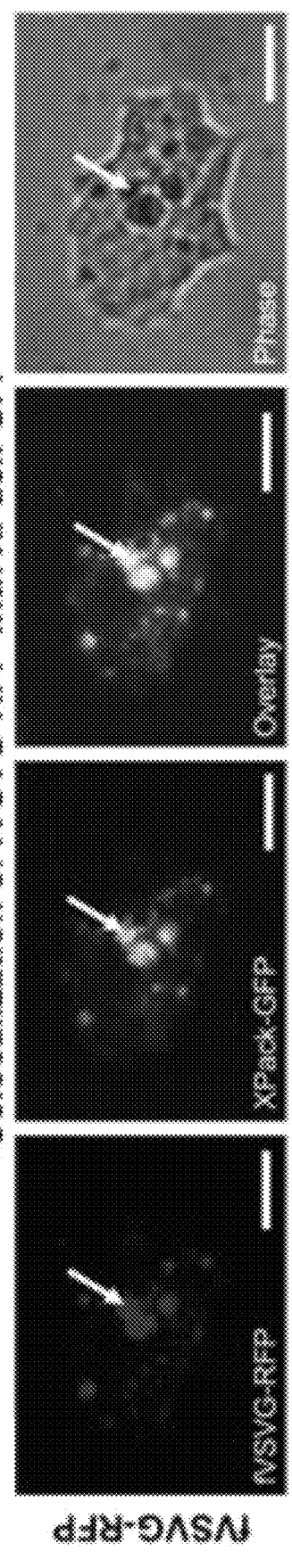
FIG. 4A
FIG. 4B

Reporter A | SP | Luciferase | mVSVG
Reporter B | SP | mVSVG | Luciferase

FIG. 5A

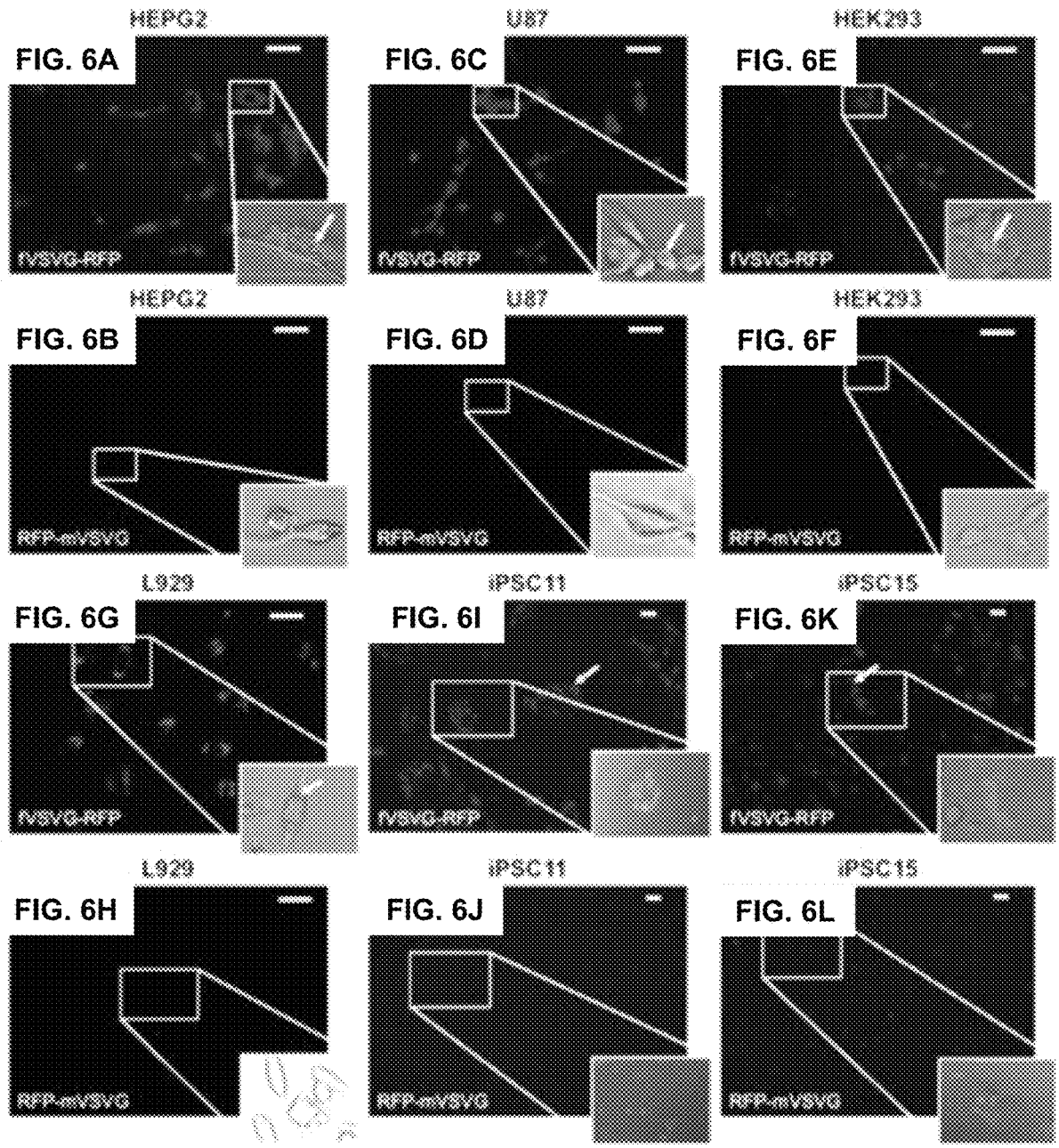

FIG. 7D

ENGINEERED EXOSOMES FOR THE DELIVERY OF BIOACTIVE CARGO USING TRANSMEMBRANE VSV-G

CROSS-REFERENCE TO RELATED APPLICATIONS

This application claims priority from U.S. Provisional Patent Application 62/531,478 filed Jul. 12, 2017, which is incorporated herein by reference.

This application is a continuation-in-part of U.S. patent application Ser. No. 15/648,215 filed Jul. 12, 2017, which is incorporated herein by reference.

U.S. patent application Ser. No. 15/648,215 filed Jul. 12, 2017 claims priority from U.S. Provisional Patent Application 62/361,295 filed Jul. 12, 2016, which is incorporated herein by reference.

FIELD OF THE INVENTION

This invention relates to delivery of bioactive cargo using engineered exosomes.

BACKGROUND OF THE INVENTION

Protein therapeutics are the fastest-growing class of US Food and Drug Administration (FDA)-approved drugs to treat the most difficult-to-manage human diseases, such as cancer, diabetes, and cardiovascular and neurologic disorders. However, the current regimen is mainly restricted to extracellular targets, due to the inability of proteins to enter cells. Exosomes, natural nanovesicles circulating in the human body, possess intrinsic ability to deliver various protein cargoes into recipient cells, thus representing an untapped source of effective delivery carrier toward intracellular targets.

Exosomes are lipid bilayer-enclosed extracellular vesicles that transport proteins, nucleic acids, and lipids between cells. In mammals, exosomes are actively released by almost all types of cells, exist in body fluids, and circulate in the blood. Exosomes are recognized and endocytosed by tissue cells via specific interactions between surface-membrane proteins, where after they deliver their molecular cargo. Therefore, they function in cell-cell communication and play important roles in immunodefense, pathogen spread, inflammation, tumor metastasis, and tissue repair. Exosomes are designed by nature to deliver a large and specific cargo of functional biomolecules, a feature that is guiding the development of exosome-based vehicles for targeted delivery of therapeutic agents. These studies, however, are impacted by gaps in our knowledge of exosome biogenesis and in approaches to engineer exosomes with a molecular cargo that enhances their uptake by target cells. The present invention advances the art by providing engineered exosomes for the delivery of bioactive cargo using transmembrane vesicular stomatitis virus glycoprotein (VSVG).

SUMMARY OF THE INVENTION

In this invention, we describe a pseudotyping approach to load exosomal membranes with reporter and targeting proteins. Pseudotyping is often used in the production of recombinant viruses and involves packaging the genetic components of the virus (DNA or RNA) with envelope proteins derived from a different virus. This approach allows one to select viral envelope proteins to alter host tropism, which may result in enhanced infection of the recombinant virus. The G glycoprotein of the vesicular stomatitis virus glycoprotein (VSVG) is used in this invention towards engineering exosomes with specific membrane-bound proteins by expressing gene-encoding VSVG fusion proteins in their mother cells. Taking advantage of the modular structure and well-defined membrane topology of VSVG, we engineered VSVG to achieve the following two biological objectives: 1) effective protein loading via terminal tagging of VSVG and 2) enhanced exosome uptake via VSVG pseudotyping. By generating exosomes that harbor a VSVG fusion with a protein that recognizes a surface biomarker on a target cell, it is then possible to generate exosomes repurposed as vehicles for intracellular delivery of functional fluorescent proteins and antibodies to diseased cells for high-contrast imaging and therapy, respectively.

In this invention, we provide the concept of a pseudotyping approach to load exosomal membranes with a cargo of reporter proteins. We designed and constructed a set of VSVG fusion reporters and validated the ability of exosome incorporation in living human cells. Our studies demonstrated successful exosome targeting and protein loading via transfection and fluorescent monitoring in living mammalian cells. By domain swapping, we subsequently identified a minimal molecular scaffold of VSVG (mVSVG) that contained sufficient signals for exosome targeting and protein loading. We further provide herein a demonstration of robust internalization of pseudotyped exosomes by a variety of cell types, including four somatic and two induced pluripotent stem (iPS) cell lines. Collectively, our invention offers a straightforward and effective approach to engineer exosomes as vehicles for enhanced delivery of protein reporters and protein therapeutics to target cells.

In one embodiment, an engineered exosome for the delivery of bioactive cargo is provided. The exosome defines an inner-vesicle space and an outer-vesicle space, and the exosome incorporates a vesicular stomatitis virus glycoprotein (VSVG) transmembrane anchoring scaffold onto the membrane of the exosome. The VSVG transmembrane anchoring scaffold has a C-terminal attachment site in the inner-vesicle space. The VSVG transmembrane anchoring scaffold further has a N-terminal attachment on the outer-vesicle space. A first peptide is or can be attached to the C-terminal attachment site of the VSVG transmembrane anchoring scaffold so that the first peptide is located in the inner-vesicle space. A second peptide is or can be attached to the N-terminal attachment site of the VSVG transmembrane anchoring scaffold so that the second peptide is located in in the outer-vesicle space. In another embodiment, the second peptide is or can be attached to the second terminal attachment site of the VSVG transmembrane anchoring scaffold so that the second peptide is located in the inner-vesicle space—a full length VSVG serves as the scaffold, and the second terminal attachment site is the N-terminus of the VSVG.

In yet another embodiment, the second peptide is or can be attached to the second terminal attachment site of the VSVG transmembrane anchoring scaffold so that to the second peptide is located in the outer-vesicle space—a truncated VSVG serves as the scaffold, and the second terminal attachment site is the N-terminus of the VSVG.

In yet another embodiment, the first peptide is an imaging protein, a protein drug, a suicide protein, an enzyme for replacement therapy.

In yet another embodiment, the second peptide is a 6×His tag for detection and purification, an imaging protein, a viral antigen epitope, a cancer antigen epitope, a single chain antibody, or a protein drug.

In still another embodiment, the second peptide is an imaging protein, a viral antigen epitope, a cancer antigen epitope, a protein drug, a suicide gene, a receptor for active biomolecules, or a therapeutic protein for replacement therapy.

LIST OF DEFINITIONS

Bioactive cargo=macromolecules namely proteins, nucleic acids, and lipids
fVSVG=full-length VSVG
RFP=red fluorescent protein
GFP=green fluorescent protein
MVB=multi-vesicular body
mVSVG=minimal VSVG
SP=signal peptide
VSVG=vesicular stomatitis virus glycoprotein

BRIEF DESCRIPTION OF THE DRAWINGS

FIGS. 1A-D show according to an exemplary embodiment of the invention a strategy of exosome pseudotyping. FIG. 1A shows membrane topology of the fVSVG. The matured fVSVG is a single transmembrane protein without the SP. The large N-terminal ectodomain (black line) with a short stem region (green line) is situated at the outer surface of the plasma membrane or the luminal side of the endosome. Those sequences are followed by a transmembrane helix and a cytoplasmic tail. FIG. 1B shows design of VSVG fusion constructs. From top to bottom, the fVSVG fused with either RFP (fVSVG-RFP) or GFP (fVSVG-GFP) at the C-terminal, the ectodomain was replaced by RFP (RFP-mVSVG), the fVSVG fused with *Gaussia* luciferase (Gluc) at the C-terminal (fVSVG-Gluc), and the ectodomain was replaced by Gluc (Gluc-mVSVG). FIG. 1C an exemplary model illustrating how VSVG participates in exosomes in a mammalian cell. Ectopic expression of VSVG occurs at the rough endoplasmic reticulum (ER) via its SP guiding, and subsequently SP-cleaved VSVG is funneled to the plasma membrane and becomes concentrated in tetraspanin (CD63)-enriched microdomains, where the first inward budding begins to form endosomes. The second inward budding from the endosome forms exosomes that are stored in a MVB prior to release into extracellular space. FIG. 1D shows a schematic illustration of the pseudotyped and protein-loaded exosome. Membrane topology of VSVG (black), loaded protein cargo GFP (green) or RFP (red), and exosome markers (CD63/CD81, blue) are indicated. Color indications or references are described in U.S. Provisional Patent Application 62/531,478 filed Jul. 12, 2017, which is incorporated herein by reference.

FIGS. 3A-I show according to an exemplary embodiment of the invention validation of minimal VSVG (mVSVG) scaffold for exosome targeting. HEK293 cells were cotransfected with RFP-mVSVG and fVSVG-GFP for 3 days. Cell images were taken by fluorescence microscopy to show the intracellular expression of mVSVG (FIG. 3A, red), fVSVG (FIG. 3B, green), and colocalization of both (FIG. 3C, yellow). Alternatively, cells were cotransfected with RFP-mVSVG and endosome marker Rab5A-GFP for 3 days. Expression and subcellular distribution were shown for mVSVG (FIG. 3D, FIG. 3G; red), Rab5A (FIG. 3E, green) and colocalization of both in overlay (FIG. 3F, yellow). Similar results were obtained to show the expression and subcellular distribution of exosome marker CD63 (FIG. 3H) and its colocalization with mVSVG (FIG. 3I, yellow). Arrows indicate endosome/exosome/MVB structures. Scale bar 20 micrometers. Color indications or references are described in U.S. Provisional Patent Application 62/531,478 filed Jul. 12, 2017, which is incorporated herein by reference.

FIGS. 4A-B show according to an exemplary embodiment of the invention time course of VSVG fusion incorporation into exosomes. HEK293 cells were transfected with fVSVG-RFP or XPack-GFP alone (an exosome tracer) for indicated periods of time. The incorporation of fVSVG into exosomes was monitored and compared with that of) (Pack. Live cell images were taken at days 1, 2, 4, and 6; representative images are shown to illustrate the expression of fVSVG (FIG. 4A, top panel) and)(Pack (FIG. 4A, bottom panel) at early membrane appearance (days 1 and 2), and final incorporation in exosomes (days 4 and 6). (FIG. 4B) In a separate set of experiments, cells were cotransfected with fVSVG-RFP and XPack-GFP for 3 days. The expression of fVSVG (red),)(Pack (green), and colocalization of both (yellow in overlay) are shown. Arrows indicate membrane locations and endosome/exosome/MVB structures. Scale bar 20 micrometers. Color indications or references are described in U.S. Provisional Patent Application 62/531,478 filed Jul. 12, 2017, which is incorporated herein by reference.

FIGS. 5A-G show according to an exemplary embodiment of the invention secretion and characterization of pseudotyped exosomes. FIG. 5A: Configuration of *Gaussia* luciferase reporters used for monitoring exosome secretion. FIG. 5B: *Gaussia* luciferase activity was assayed using conditioned media from HEK293 cell culture on day 2 posttransfection, with mock transfection as negative controls. Data presented as relative light units from three experiments (mean standard deviation, n3). FIG. 5C: Immunological pull-down of pseudotyped exosomes using CD81-specific antibody (Ab)-coated beads. Both images of green fluorescence and phase contrast are displayed to show GFP-positive anti-CD81 antibody-precipitated exosomes. Non-Ab-coated beads were included as controls. Arrows indicate exosome-positive beads. FIGS. 5AD-F: Nanoparticle-tracking analysis profiles off VSVG, mVSVG, or CD63 pseudotyped exosomes isolated from HEK293 cells at 3 days posttransfection, showing average sizes of respective exosomes. FIG. 5G: There was no difference in average exosome size between pseudotyped fVSVG-RFP/RFP-mVSVG and modified CD63 (an endogenous exosome marker). Color indications or references are described in U.S. Provisional Patent Application 62/531,478 filed Jul. 12, 2017, which is incorporated herein by reference.

FIGS. 6A-L show according to an exemplary embodiment of the invention exosome uptake in mammalian cells. Uptake of pseudotyped exosomes in various cell lines (HEPG2, U87, HEK293, L929, iPSC11, and iPSC15) was compared between fVSVG and mVSVG. Cultured cells were treated with either fVSVG-RFP or RFP-mVSVG in a 96-well plate. Enhanced uptake of fVSVG was evident (FIGS. 6A-C and FIGS. 6G-K) compared to mVSVG (FIGS. 6D-F and FIGS. 6II-L). Following exosome incubation for 48 hours, images were taken with fluorescent microscopy at 20× magnification for HEPG2, U87, HEK293, and L929 cells (scale bar 20 m). For iPSC11 and iPSC15 cells, images were taken after exosome incubation for 24 hours at 10× magnification (scale bar 10 micrometers). Arrows point to internalized RFP-labeled exosomes. Color indications or references are described in U.S. Provisional Patent Application 62/531,478 filed Jul. 12, 2017, which is incorporated herein by reference.

FIGS. 7A-D show according to an exemplary embodiment of the invention quantification of exosome uptake in HEK293 cells by flow cytometry. Recipient cells were loaded with either fVSVG-RFP or RFP-mVSVG pseudotyped cell-sorting analysis. Right shifts in fluorescence signals for both fVSVG (FIG. 7C) and mVSVG (FIG. 7B) exosomes are shown in comparison with the negative control (FIG. 7A) and in panel (FIG. 7D), indicating an enhancement (9.7-fold) in exosome uptake by pseudotyping in HEK293 cells. Color indications or references are described in U.S. Provisional Patent Application 62/531,478 filed Jul. 12, 2017, which is incorporated herein by reference.

DETAILED DESCRIPTION

Materials and Methods
Cell Culture

Human embryonic kidney cells (HEK293) were purchased from Alstem (Richmond, Calif., USA). Human glioblastoma cells (U87), human liver cancer cells (HEPG2), and mouse adipose tissue fibroblast cells (L929) were purchased from the American Type Culture Collection (Manassas, Va., USA). All cells were maintained in high-glucose Dulbecco's Modified Eagle's Medium supplemented with 10% fetal bovine serum, 2 mM GlutaMax (Thermo Fisher Scientific, Waltham, Mass., USA), and 100 U/mL penicillin—streptomycin. At 80%-90% confluence, cells were treated with 0.25% trypsin-ethylenediaminetetraacetic acid for dissociation and passed at a ratio of 1:4. Human iPS cells (iPS11 and iPS15) were purchased from Alstem. These lines have been preadapted to feeder-free conditions and maintained in serum-free mTeSR1 medium (Stemcell Technologies, Vancouver, BC, Canada) supplemented with 100 U/mL penicillin—streptomycin. All cells were incubated at 37 C in 5% $CO_2$.

Cell Transfection

All transfections were performed in six-well plates unless otherwise stated. At 60%-70% confluence, cells were transfected by plasmid DNA (1-2.5 g/well) mixed with either Lipofectamine (Thermo Fisher Scientific) or FuGene 6 transfection reagent (Promega, Fitchburg, Wis., USA).

Design and Construction of Expression Vectors for VSVG Fusion Proteins

Figure 1A:
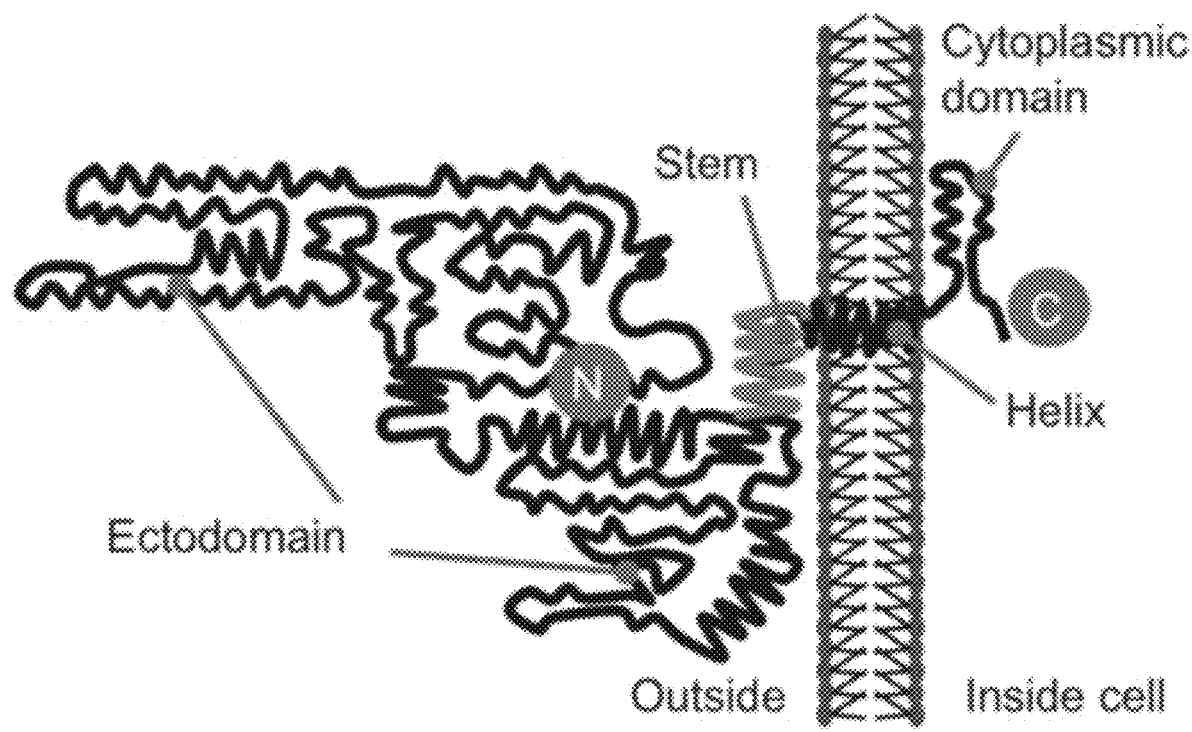

Full-length VSVG (fVSVG) gene-encoding single-transmembrane protein was used for making various fusion constructs (FIG. 1A and FIG. 1B). Fusion constructs were configured 5'→3' as per the following: a constitutive cytomegalo-virus promoter, the signal peptide (SP), an in-frame insertion of red fluorescent protein (RFP) or *Gaussia* luciferase (Gluc), the stem sequence, transmembrane helix, the cytosolic tail, followed by an in-frame RFP, GFP, or Gluc lacking the endogenous SP sequences, and a stop codon (FIG. 1B). A polyadenylation signal was added at the 3' end. The construction of these fusion protein expression vectors was conducted using a combination of polymerase chain reaction amplification for individual fragments and subsequently seamless joining by enzymes from System Biosciences (Palo Alto, Calif., USA). To display an RFP or Gluc on the outer surface of exosomes, the ectodomain of VSVG was swapped with indicated reporter proteins. To load RFP, GFP, or Gluc inside exosomes, these sequences were inserted at the end of the cytoplasm tail of VSVG (FIG. 1B). Construction of both exosomes (CD63-GFP, CD81-GFP) and endosome markers (GFP-Rab5a) has been shown by the inventors (Stickney et al. Development of exosome surface display technology in living human cells. *Biochem Biophys Res Commun.* 2016; 472(1):53-59). A positive exosome tracer, XPack-GFP, was purchased from System Biosciences. All final constructs were confirmed by double-stranded DNA sequencing (Elim Biopharmaceuticals, Hayward, Calif., USA). Sequences of fVSVG and its fusion proteins were also provided (Supplementary materials).

Pseudotyping and Preparation of Exosomes

Pseudotyping and subsequent preparation of exosomes from culture cells were performed as described by the inventors (Stickney et al. Development of exosome surface display technology in living human cells. *Biochem Biophys Res Commun.* 2016; 472(1):53-59). Briefly, HEK293 cells grown on 15 cm plates (70%-80% confluence) were transfected with FuGene transfection reagent. At 24 hours after transfection, cells were switched to serum-free UltraCulture medium (Lonza, Basel, Switzerland) for the production of pseudotyped exosomes. After 48 hours, the conditioned medium was collected and centrifuged at 1,500 g for 5 minutes, then subjected to ultrafiltration with a 0.22 m filter. The filtered medium was subsequently mixed with Exo-Quick-TC (System Biosciences), followed by centrifugation at 3,000 g for 30 minutes at 4 degrees Celsius. The enriched exosome pellet was resuspended in a phosphate buffer and stored at 80 degrees Celsius for future use. The protein concentration of prepared exosomes was measured by Nano-Drop Lite (Thermo Fisher Scientific).

Luciferase Assay

A Gluc assay was conducted as previously reported (Afshari et al. A cooled CCD camera-based protocol provides an effective solution for in vitro monitoring of luciferase. *Biochem Biophys Res Commun.* 2015; 458(3):543-548) Briefly, the conditioned medium was collected and centrifuged at 1,500 g for 5 minutes. In a typical experiment, 20 microLiters of conditioned medium containing the modified exosomes was analyzed for Gluc activity using a Synergy HT multi-mode microplate reader (BioTek Instruments, Winooski, Vt., USA). Data are presented as relative light units for comparison.

Exosome Pull-Down Assay

An exosome pull-down assay was conducted using an Exo-Flow kit (System Biosciences). Briefly, 20 microLiters of streptavidin-coupled magnetic beads was mixed with 15 microLiters of biotin-labeled CD81 antibody for 2 hours at 4 degrees Celsius. The beads were then washed, and 50 micrograms of pseudotyped exosomes was incubated overnight with the antibody-captured beads. These exosome pull-down beads were then washed extensively and transferred to clear wells of a 96-well plate prior to imaging. Beads without CD81 antibodies were used as negative controls.

Nanoparticle-Tracking Analysis (NTA)

Exosomes isolated from transfected cells were subjected to NTA using an NS300 machine (Malvern Instruments, Malvern, UK). In a typical analysis, 1 mL of the diluted exosomes (1:1,000 dilutions) was used for exosome visualization by laser-light scattering, and three videos of 60 seconds each were recorded. Data analysis was performed by NTA software, and the results are presented graphically to show particle size and distribution.

Exosome Uptake Assay

Recipient cells were seeded in a 96-well plate and incubated with exosomes as indicated in each experiment. Briefly, nonstem cells at 20%-30% confluence were loaded with 5 micrograms exosome protein/well in serum-free UltraCulture medium. Cells were then imaged at 20 magnification using fluorescence microscopy (DMI3000B; Leica Microsystems, Wetzlar, Germany). For iPS cell lines, cells were cultured on a Matrigel-coated plate and loaded with exosomes in serum-free mTeRS1 medium. After an extensive wash, loaded iPS cells were imaged at 10 magnifications using an Evos FL autofluorescence microscope. Microscopic imaging parameters (exposure time, contrast, and gain) were the same for all experiments.

Fluorescence-Activated Cell-Sorting Analysis

HEK293 or U87A cells were sorted and quantified using flow cytometry (Accuri C6; BD Biosciences, San Jose, Calif., USA) following a 2-day transfection. Events (10,000-30,000) were recorded for each sample using an FL3A channel to detect the fluorescence of RFP. Fluorescence-activated cell-sorting data were analyzed with CFlow Plus software (BD Biosciences).

Live Cell Microscopy

Images were typically taken on live cells using fluorescence microscopy. To show the intracellular localizations of the fluorescent fusion proteins, fluorescent and phase-contrast images were adjusted for brightness and contrast or overlaid using Adobe Photoshop CS. Whenever for quantitative comparison, all imaging data were obtained using identical parameters (exposure time, contrast, and gain).

Results

Experimental Design and Pseudotyping Strategy

Figure 1C:
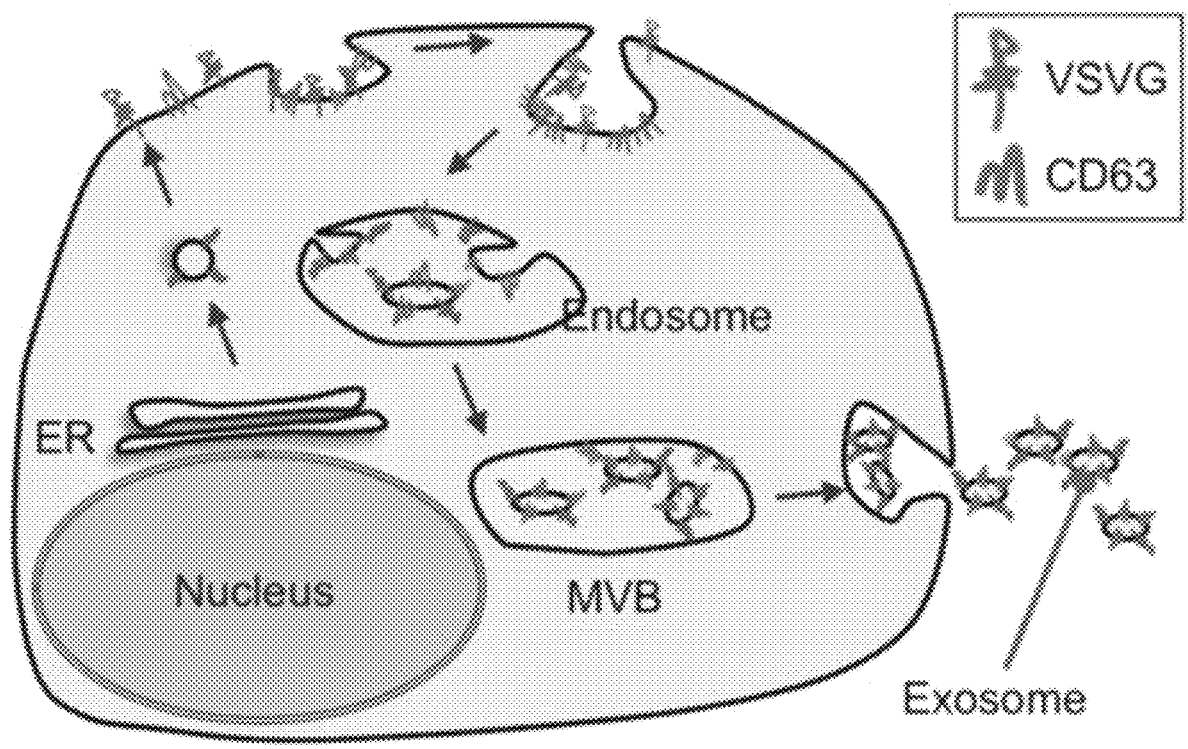
Figure 1D:
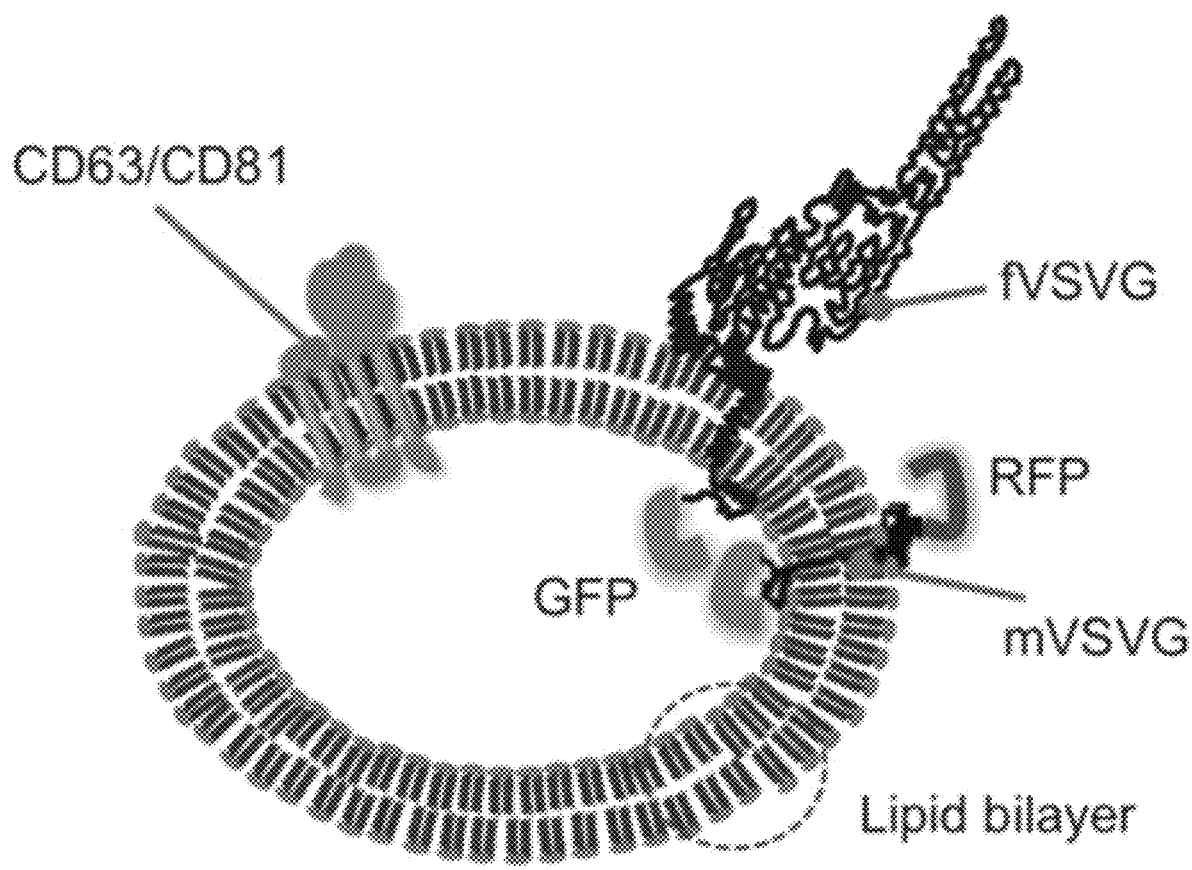

First, we developed a strategy to repurpose exosomes as vehicles for in vivo targeted delivery and imaging of protein-based therapeutics and fluorescent probes. Key to the success of our pseudotyping approach was to control the topology of VSVG on the exosome membrane. We hypothesized that the preferred topology of VSVG on the exosome would be one where the VSVG protein is retained in the membrane by the interaction of its hydrophobic tail with the bilayer membrane. This anchoring strategy would position the ectodomain of fVSVG to the outer surface of the exosome for pseudotyping (FIG. 1A and FIG. 1D). Moreover, by fusing targeting molecules to fVSVG, one could maximize interactions of the exosome with surface antigens on the plasma membrane of a target cell. Alternatively, by swapping the ectodomain with a cell-trophic peptide or a disease-targeting antibody, one could target the exosome to a specific tissue or tumor. This latter approach could be further refined for in vivo targeted therapy and imaging of tumors or diseased tissue by fusing an engineered antibody or a near-infrared fluorescent protein.

To test this new approach, we constructed several fusion proteins composed of fVSVG with fluorescent or luminescent reporters by way of domain swapping and protein tagging. To ensure these fusion proteins were properly anchored with the correct topography on exosomal membranes, the SP sequences and the transmembrane helix of fVSVG were left intact in all fusion proteins (FIG. 1B). This strategy would limit the synthesis of VSVG to the surface of the rough ER, with the SP sequence guiding the insertion of the ectodomain into the ER lumen (FIG. 1C). In a later section of the manuscript, we show this strategy correctly positions the transmembrane helix of VSVG fusion proteins in the membrane of HEK293 cells, with the C-terminal tail projecting into the cytoplasm. It has been shown that the SP sequence is removed and the remaining VSVG molecules concentrate in tetraspanin-enriched microdomains of the plasma membrane. Exosomes are believed to form these domains in two sequential inward-budding processes: the first generates an endosome, while the second leads to the formation of multiple-vesicle bodies that eventually release individual exosomes into the extracellular space (FIG. 1C).

VSVG Introduces Functional Fluorescent Proteins to Presecreted Exosomes

Figure 2I:
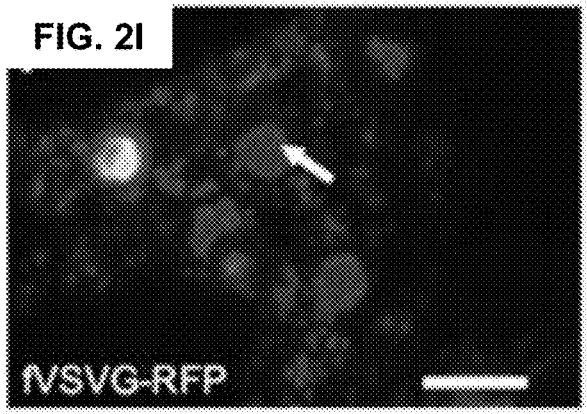
FIGS. 2A-N show according to an exemplary embodiment of the invention fluorescent imaging of VSVG fusion proteins in HEK293 cells. Cultured cells were transfected with either fVSVG-GFP/fVSVG-RFP alone or in combination with Rab5A-GFP/CD63-GFP for indicated periods of time. Cell images of fluorescence signal and phase contract of the same field were taken to show the expression and an earlier plasma membrane distribution of fVSVG-GFP on day 2 (FIG. 2A, green.
FIG. 2B, overlay), and late-punctate intracellular localization on day 3 (FIG. 2C, green.
FIG. 2D, overlay). Similarly, the expression and subcellular localization of fVSVG are shown in red (FIGS. 2E-H). Interestingly, following cotransfection of cells with fVSVG-RFP and Rab5A-GFP (an endosome marker) for 3 days, images show the expression and cellular distribution of fVSVG (FIG. 2I, red), Rab5A (FIG. 2J, green), or colocalization of both (FIG. 2K, yellow). Alternatively, cotransfection with both fVSVG-RFP and CD63-GFP (an exosome marker) resulted in similar patterns of expression and cellular distribution for fVSVG (FIG. 2L, red), CD63 (FIG. 2M, green), and colocalization of both (FIG. 2N, yellow). Arrows indicate endosome/exosome/MVB structures. Scale bar 20 micrometers. Color indications or references are described in U.S. Provisional Patent Application 62/531,478 filed Jul. 12, 2017, which is incorporated herein by reference.

Next, we examined if the proteins we appended to VSVG were functional and correctly positioned on the exosomal membrane. First, we generated two fusion proteins tagged with GFP or RFP at the C-terminus of VSVG. Cultured HEK293 cells were transfected with these constructs, and their intracellular localization expression was recorded for up to 7 days by fluorescence microscopy. Analysis of these image data shows accumulations of fluorescent proteins at plasma membranes of HEK293 cells within 2 days of the transfection (FIG. 2A and FIG. 2E). The membrane localization of these fluorescent proteins was evident when comparing fluorescence signals with the phase contrast in merged images (FIG. 2B and FIG. 2F). By day 3, the fluorescence signal of the fusion protein was found at other intracellular regions of the cell (FIG. 2C and FIG. 2G). The punctate intracellular fluorescence was consistent with that expected for endocytic structures (FIG. 2D and FIG. 2H). We argue the intracellular puncta represent endosomes and are formed by the inward budding of the plasma membrane.

Next, we conducted imaging studies to verify the fluorescence of VSVG fusion expressed in HEK293 cells colocalized to endocytic compartments by comparing distributions of VSVG fluorescence with validated fluorescent markers of the endosome. These studies, conducted in cells cotransfected with fVSVG-RFP (red) and an endosome marker, Rab5A-GFP (green), showed considerable overlap of the two fluo-rescent signals that was immediately apparent by the large number of yellow puncta in overlaid images (FIGS. 2I-K) and provide compelling evidence that fluorescent fVSVG fusion protein localizes to endosomes.

Figure 2L:
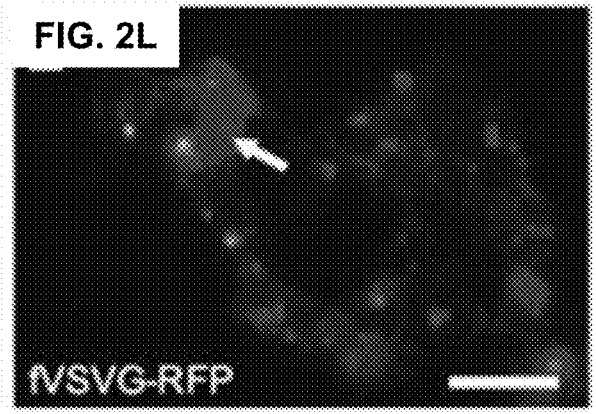
Figure 2J:
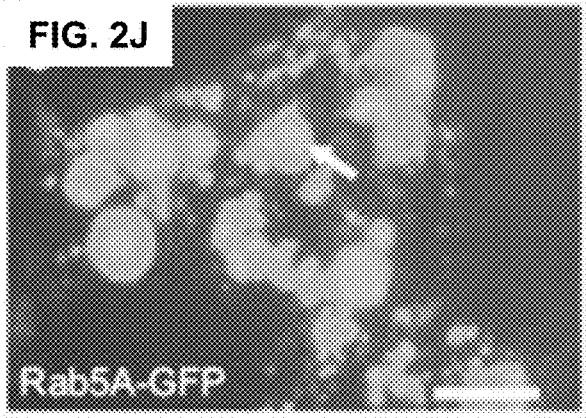
Figure 2M:
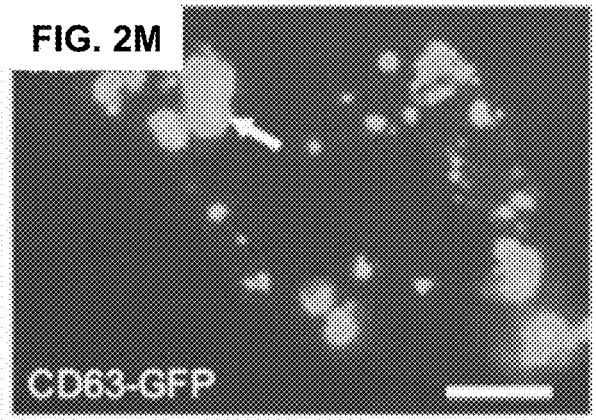
Figure 2K:
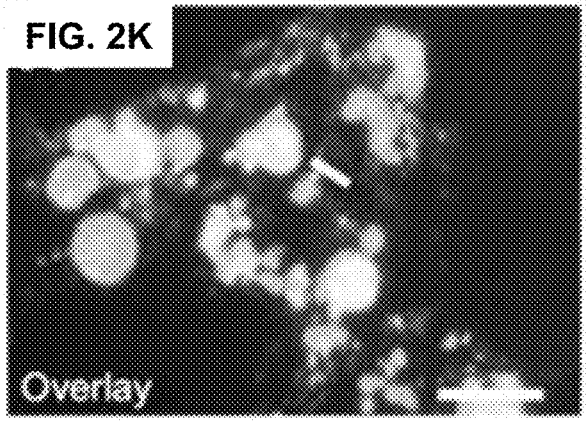
Figure 2N:
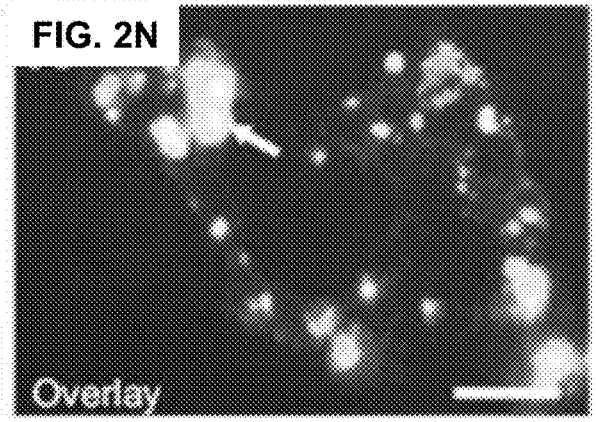

Next, we conducted studies to show fluorescent endosomal vesicles were components of the exosome biogenesis pathway. We cotransfected HEK293 cells with fVSVG-RFP (red) and CD63-GFP (green), a validated marker of exosomes. High-resolution fluorescence imaging of cells transfected with these two constructs also revealed extensive overlap of the green and red fluorescence signals, which can be appreciated in merged images that highlight overlapping signals in yellow (FIGS. 2L-N). These results confirm the expectation that fVSVG participates in the biogenesis of the endocytic compartment as presecreted exosomes.

Together, the results of these imaging studies are consistent with our hypothesis that fVSVG serves as a molecular scaffold that both integrates and correctly projects appended proteins, including RFP, in the exosomal membrane. The readily detectable fluorescence of RFP suggests that protein payloads on fVSVG are functional, and protein integration into the exosome membrane is highly efficient.

Identification of the minimal VSVG scaffold for exosome targeting fVSVG is a single transmembrane glycoprotein that is characterized by a spike that protrudes on the outer face of the viral particle. In the present study, fVSVGs are shown to integrate into exosome membranes, with the ectodomain projecting from the external face. The ectodomain of fVSVG recognizes specific proteins on the surface of recipient cells and facilitates attachment and internalization. We asked whether mVSVG, a construct that lacks the ectodomain, is sufficient to anchor the protein to the exosomal membrane. In these studies, the ectodomain was replaced with RFP, although the fusion protein contained the N-terminal SP (54aa) and the C-terminal domain (70aa) (FIG. 1B). We recorded images of the red fluorescence of RFP-mVSVG in transfected HEK293 cells. The red fluorescence localized to the same type of puncta we found for mVSVG fusion proteins that were identified as potentially endocytic com-partments (FIG. 3A, FIG. 3D and FIG. 3G). Importantly, we found extensive overlap of the red and green fluorescence signals in cells cotransfected with RFP-mVSVG and each of the fluorescent fusion proteins fVSVG-GFP (FIG. 3B and FIG. 3C), Rab5A-GFP (an endosome marker, FIG. 3E and FIG. 3F), CD63-GFP (an exosome marker, FIG. 3H and FIG. 3I), and CD81-GFP (FIG. S1 as shown in Appendix A in U.S. Provisional Patent Application 62/531,478 filed Jul. 12, 2017, which is incorporated herein by reference), strongly suggesting endosome/exosome participation. These data identify the SP domain and the C-terminus of VSVG as the "minimal" scaffold of VSVG for exosome targeting.

VSVG Incorporation into Exosomes Via Endogenous Pathway

Next, we examined how VSVG is incorporated into exosomes in HEK293 cells by recording the kinetics of fVSVG and)(Pack exosome-tracer participation into exosomes. After their transfection in HEK293 cells, the fluorescence of RFP-fVSVG and XPack-GFP was recorded as a function of time in live cells. These imaging studies conformed with initial findings on the early appearance of RFP at the plasma membrane (FIG. 4A, upper panel, days 1 and 2) and late participation of fVSVG-RFP in intracellular granules, tentatively assigned as exosomes (FIG. 4A, upper panel, days 4 and 6). Analysis of the corresponding images of XPack-GFP showed a similar temporal pattern (FIG. 4A, lower panel), which would suggest that fVSVG and)(Pack share a common pathway in exosome biogenesis. After cotransfection, analysis of fluorescence images of these two independent fluorescent tracers revealed extensive colocalization (FIG. 4B), indicating they shared similar intracellular distribution in HEK293 cells. These findings support our hypothesis that VSVG is preferentially recruited into exosomes via the endocytic pathway.

To explore whether the incorporation of VSVG into exosomes is a general phenomenon, we transfected VSVG-reporter proteins into three additional cell lines: U87, HEPG2, and L929. The distribution of fVSVG-RFP was recorded dynamically in each type of living cell using fluorescence microscopy. These studies showed the fVSVG fusion protein localizes to punctate structures in all three cell types and strongly suggests that fVSVG plays a common role in exosome biogenesis in a variety of human cell types (FIG. S2A as shown in Appendix A in U.S. Provisional Patent Application 62/531,478 filed Jul. 12, 2017, which is incorporated herein by reference). Moreover, we found that the intracellular pattern of RFP-mVSVG was similar to fVSVG in the addi-tional cell lines (FIG. S2B as shown in Appendix A in U.S. Provisional Patent Application 62/531, 478 filed Jul. 12, 2017, which is incorporated herein by reference). Together, our data show that fVSVG and mVSVG are capable of targeting and introducing functional fusion proteins into exosomal membranes in human and murine cells.

Characterization of Pseudotyped Exosomes Released from Transfected Cells

Figure 5B:
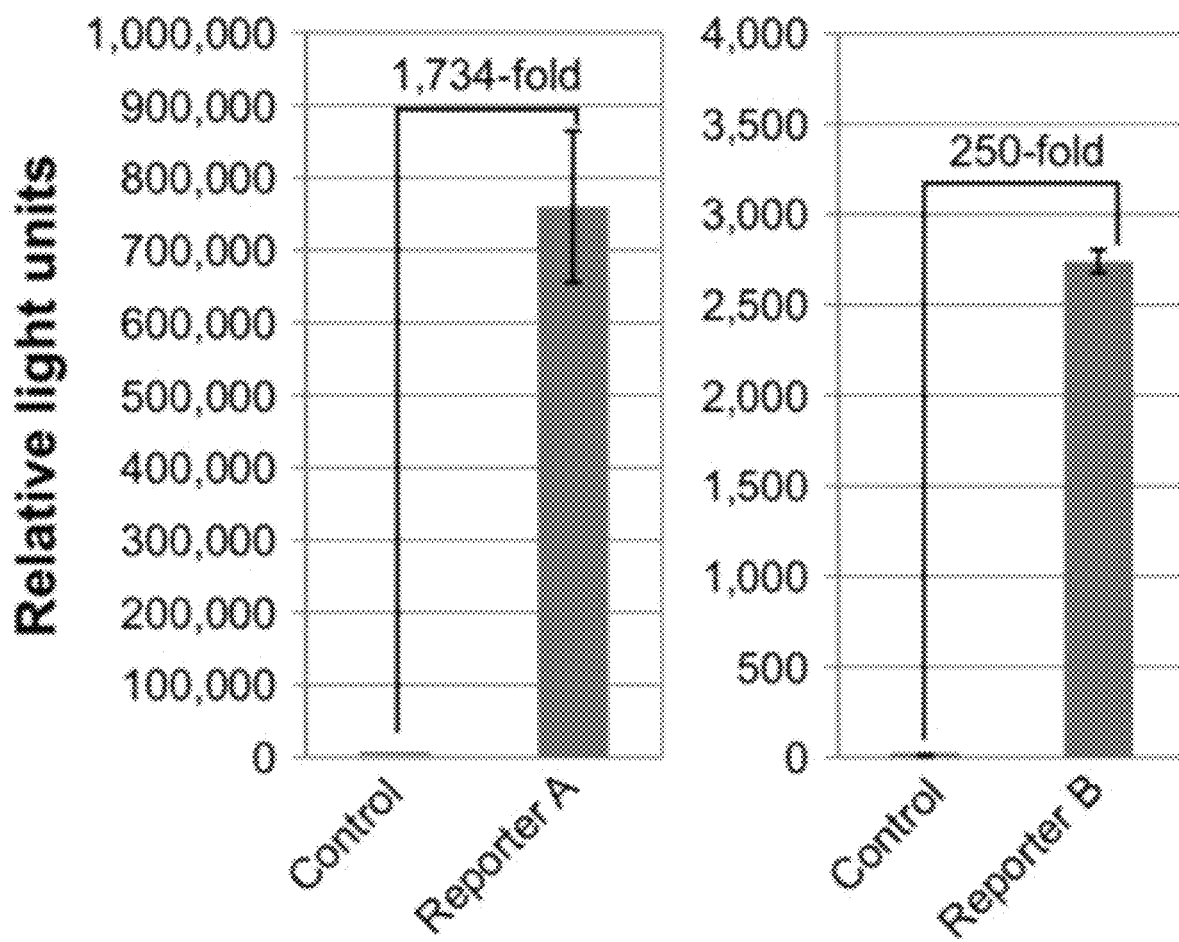

Next, we asked if VSVG-pseudotyped exosomes were released from their producing cell to the extracellular space. First, we constructed two additional VSVG reporters: mVSVG and fVSVG fusions of the highly luminescent luciferase from *Gaussia princeps* (FIG. 5A). If the pseudotyped exosomes are released from transfected cells, high levels of luciferase activities could be expected from the conditioned medium. As predicted, we detected high levels of luciferase in conditioned medium: 1,734-fold and 250-fold higher for Gluc-mVSVG and fVSVG-Gluc, respectively, compared to those of the untransfected controls (FIG. 5B). The difference in the activity of the transfected luciferase fusion proteins for these two reporters could arise from the limited availability of the coelenterazine substrate, since the Gluc-mVSVG is on the outer surface of the exosome, and hence it is more accessible to the substrate. Nevertheless, these results suggest fVSVG/mVSVG carry their appended luciferase onto exosomes in an active form, and in both cases the exosomes are released into the extracellular space.

Figure 5C:
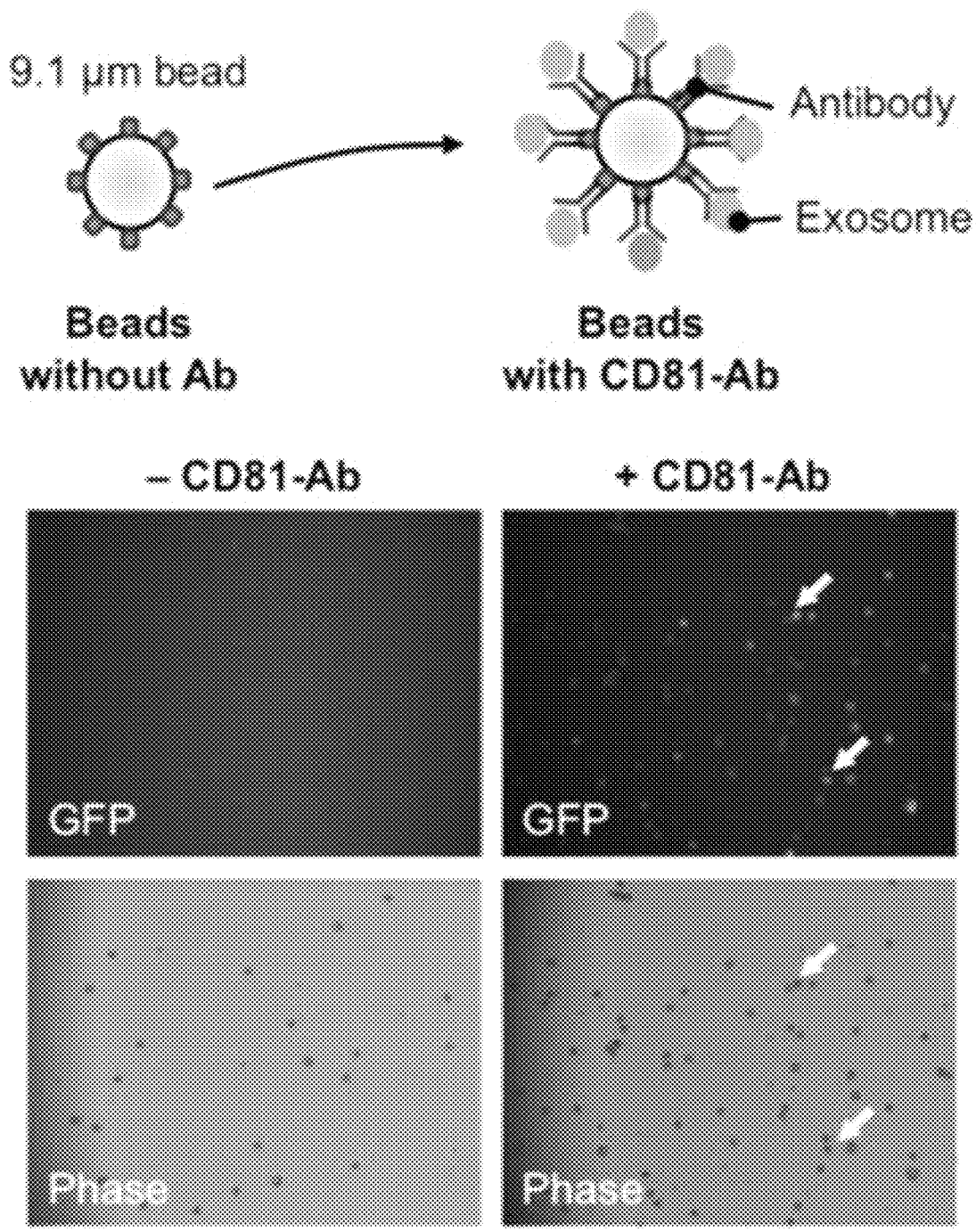

Next, we provided further confirmation that the VSVG-pseudotyped vesicles produced by HEK293 cells are true exosomes. In these studies, exosomes were pulled down from suspensions using an anti-CD81 (an exosome marker) antibody. Since the immunoprecipitated complex in the pull-downs emitted strong GFP fluorescence, we are quite certain they contained fVSVG-GFP, while the presence of CD81 confirmed they were exosomes (FIG. 5C).

Figure 5D:
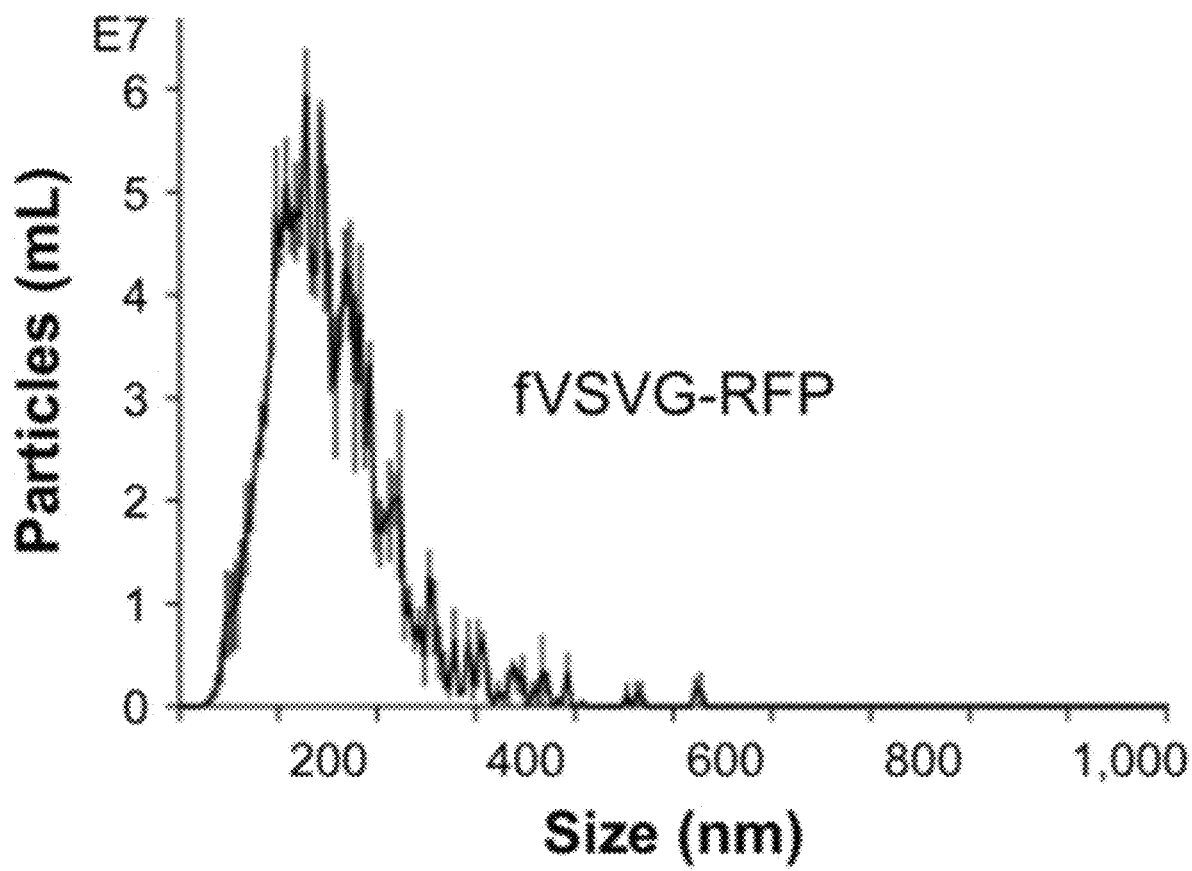
Figure 5E:
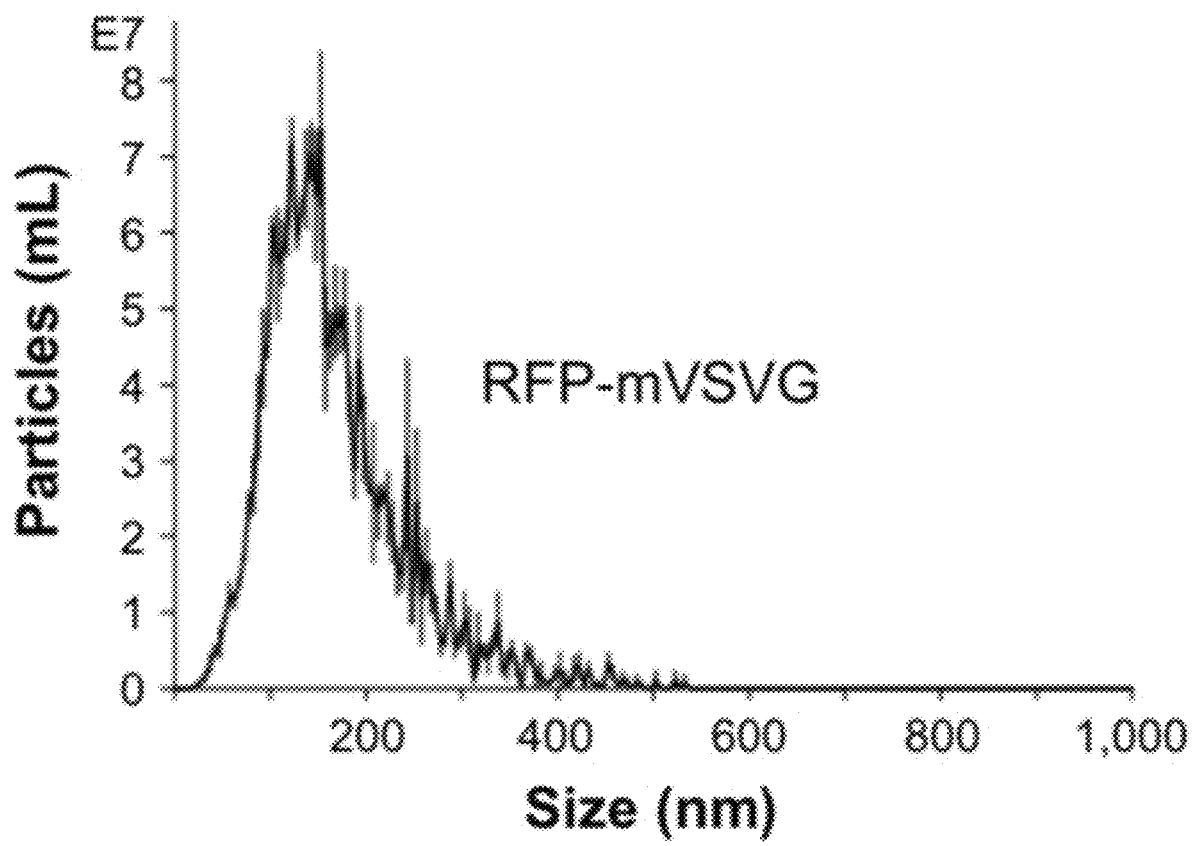
Figure 5F:
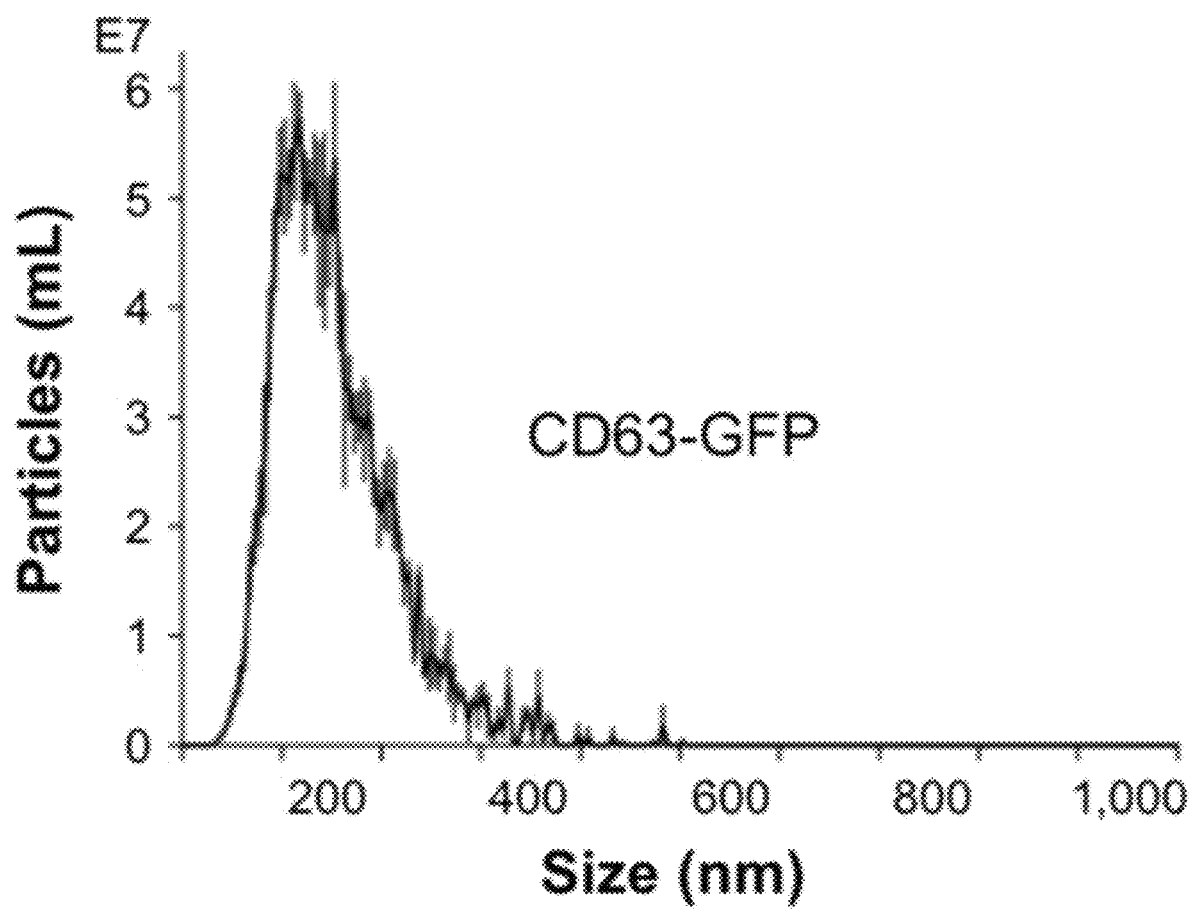
Figure 5G:
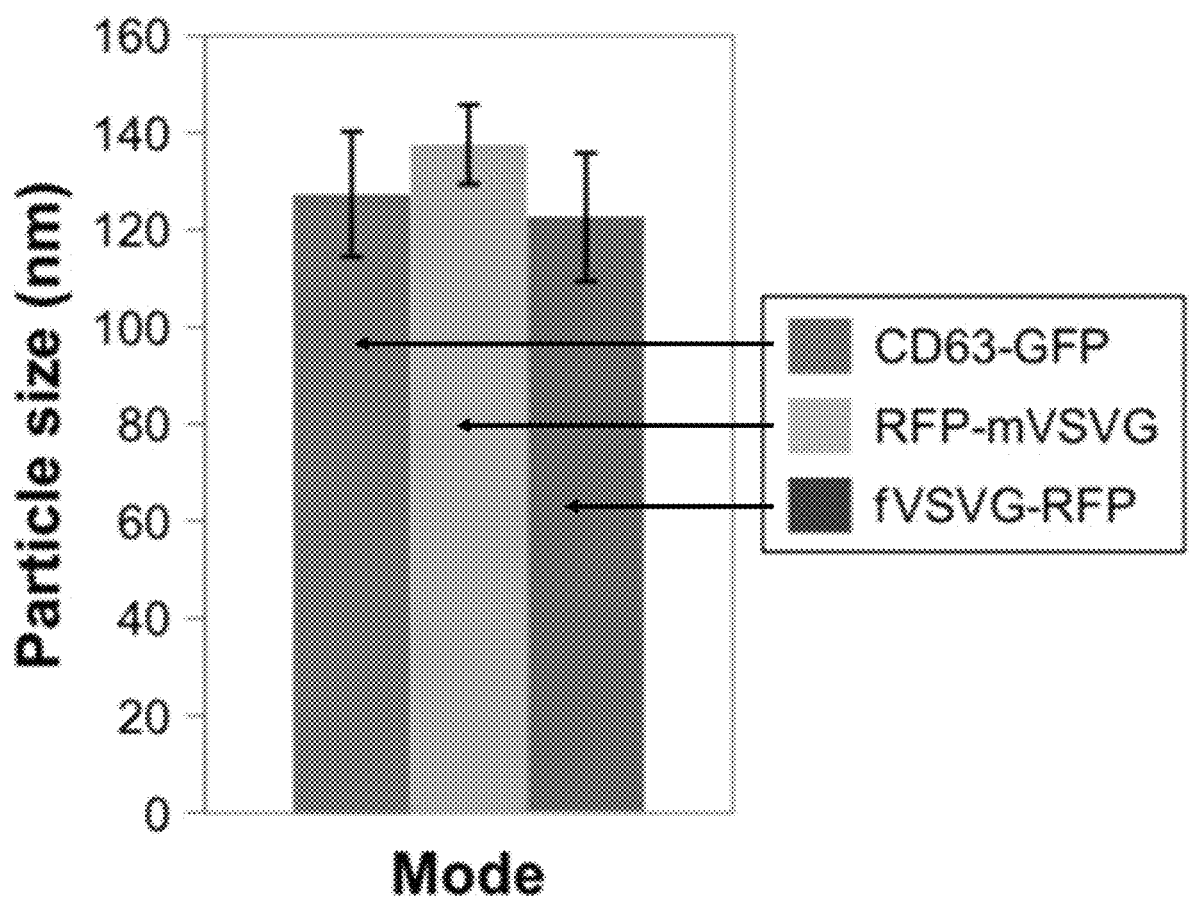

Next, we asked if the differential pseudotyping of exosomes affected their physical properties. In particular, NTA of a suspension of exosomes was assessed using the NS300. The average diameters of pseudotyped exosomes integrated with fVSVG-RFP and RFP-mVSVG were similar (FIG. 5D and FIG. 5E) and did not differ significantly from the average size determined for CD63-GFP, which acted as a control particle for these studies (FIG. 5F and FIG. 5G).

Pseudotyping Increases Exosome Uptake by Recipient Cells

We next studied the uptake of VSVG-pseudotyped exosomes by recipient cells. A key question is whether the ectodomain of VSVG may modulate the binding and uptake of exosomes. In this set of studies, we compared the binding and uptake of exosomes pseudotyped with fVSVG versus mVSVG. The delivery of the two classes of engineered exosomes to target cells was determined by imaging the distribution of intracellular red fluorescence in HEK293, HEPG2, U87, and L929 cells after incubation with the RFP-labeled exosomes (5 microgram/well). Cells incubated with purified exosomes for 48 hours were imaged using fluorescence microscopy.

Approximately 95% of HEPG2, U87, and HEK293 cells showed strong perinuclear fluorescence due to the uptake of RFP-fVSVG-loaded exosomes (FIG. 6A, FIG. 6C, FIG. 6E and FIG. 6G). On the other hand, only weak red fluorescence was recorded after incubating the same cell types with mVSVG-modified exosomes (FIG. 6B, FIG. 6D, FIG. 6F and FIG. 6H). These results led to two important conclusions: first, exosome delivery to recipient cells is enhanced by fVSVG pseudotyping, and second the ectodomain of fVSVG plays an important role in the binding and subsequent uptake of exosomes by recipient cells.

Encouraged by the observations just described, we examined exosome uptake in more complex cell types, including human iPS cells, which are notoriously difficult to transfect using standard transfection protocols. Fluorescence images of iPS cells incubated with a fixed number of fVSVG-RFP-pseudotyped exosomes for 24 hours showed strong intracellular fluorescence in 50%-60% of iPSC11 and 40%-50% of iPSC15 cells (FIG. 6I and FIG. 6K). Notably, the highest levels of exosome uptake were found in cells at the periphery of stem cell colonies, suggesting the metabolic status of highly proliferating cells may influence exosome uptake. As expected, mVSVG-loaded exosomes were found to be taken up at low levels in iPS cells, confirming our earlier finding that the pseudotyping (ectodomain) domain is critical for effective attachment and internalization by recipient cells.

Figure 7A:
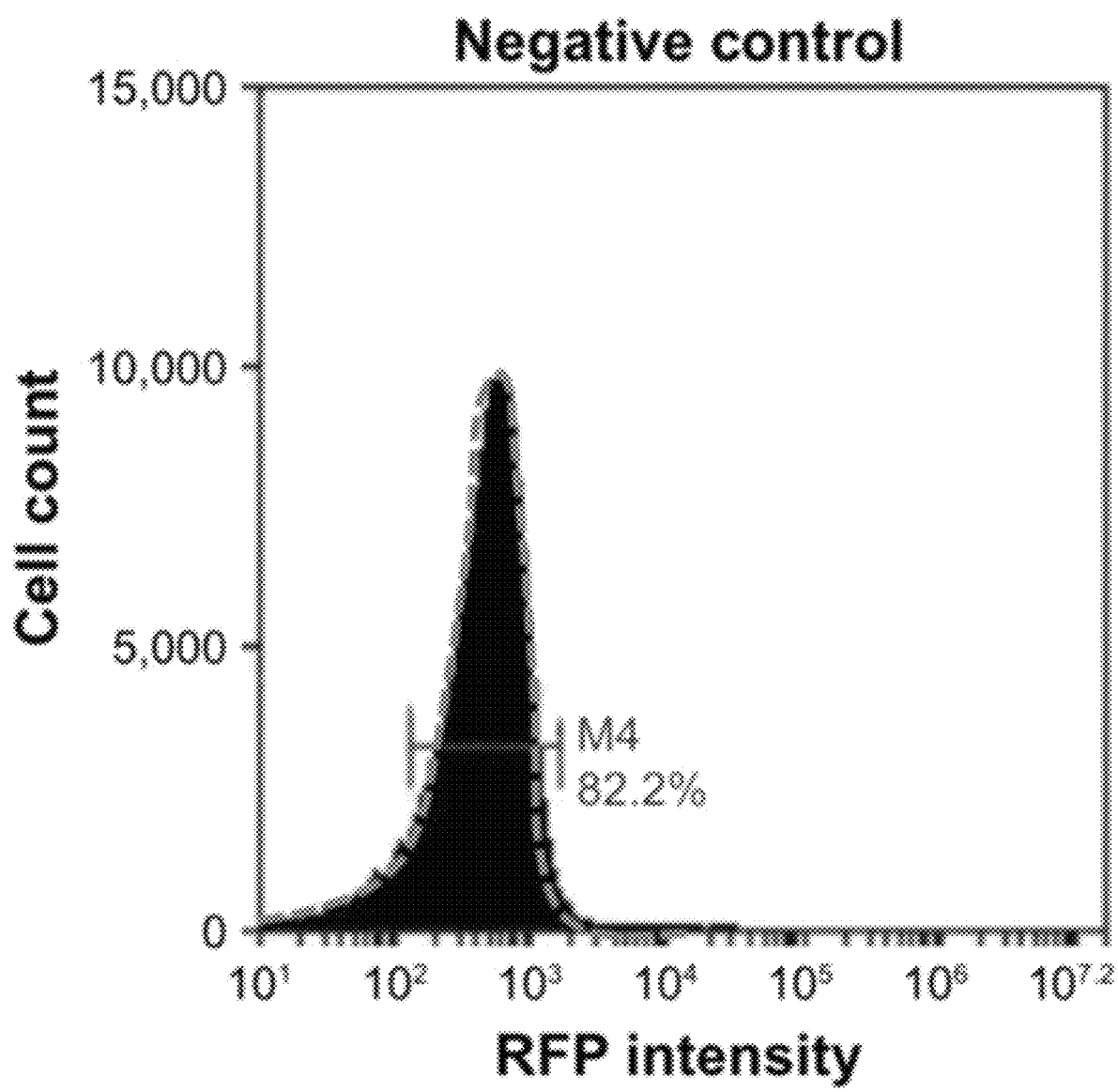
Figure 7B:
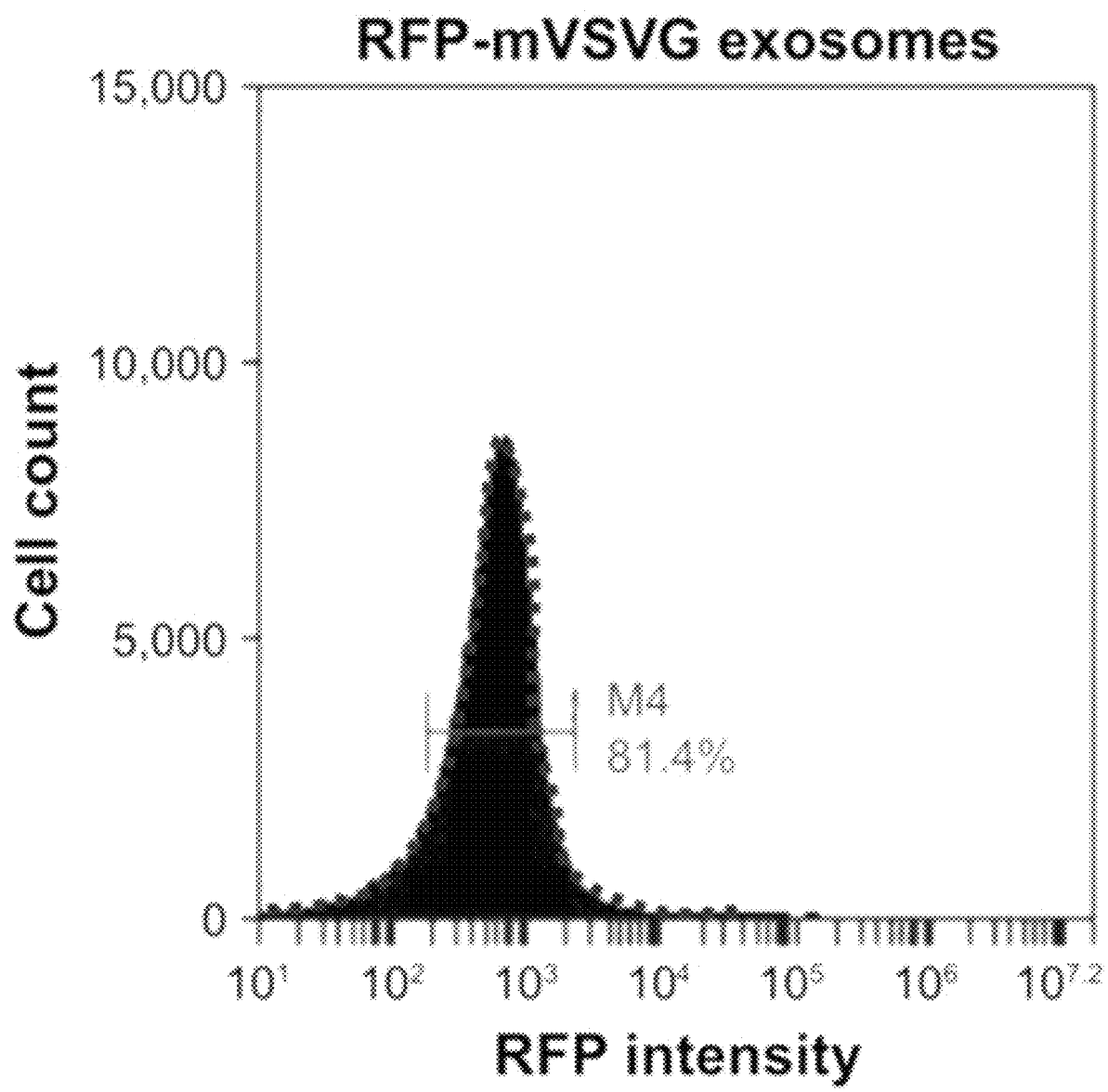
Figure 7C:
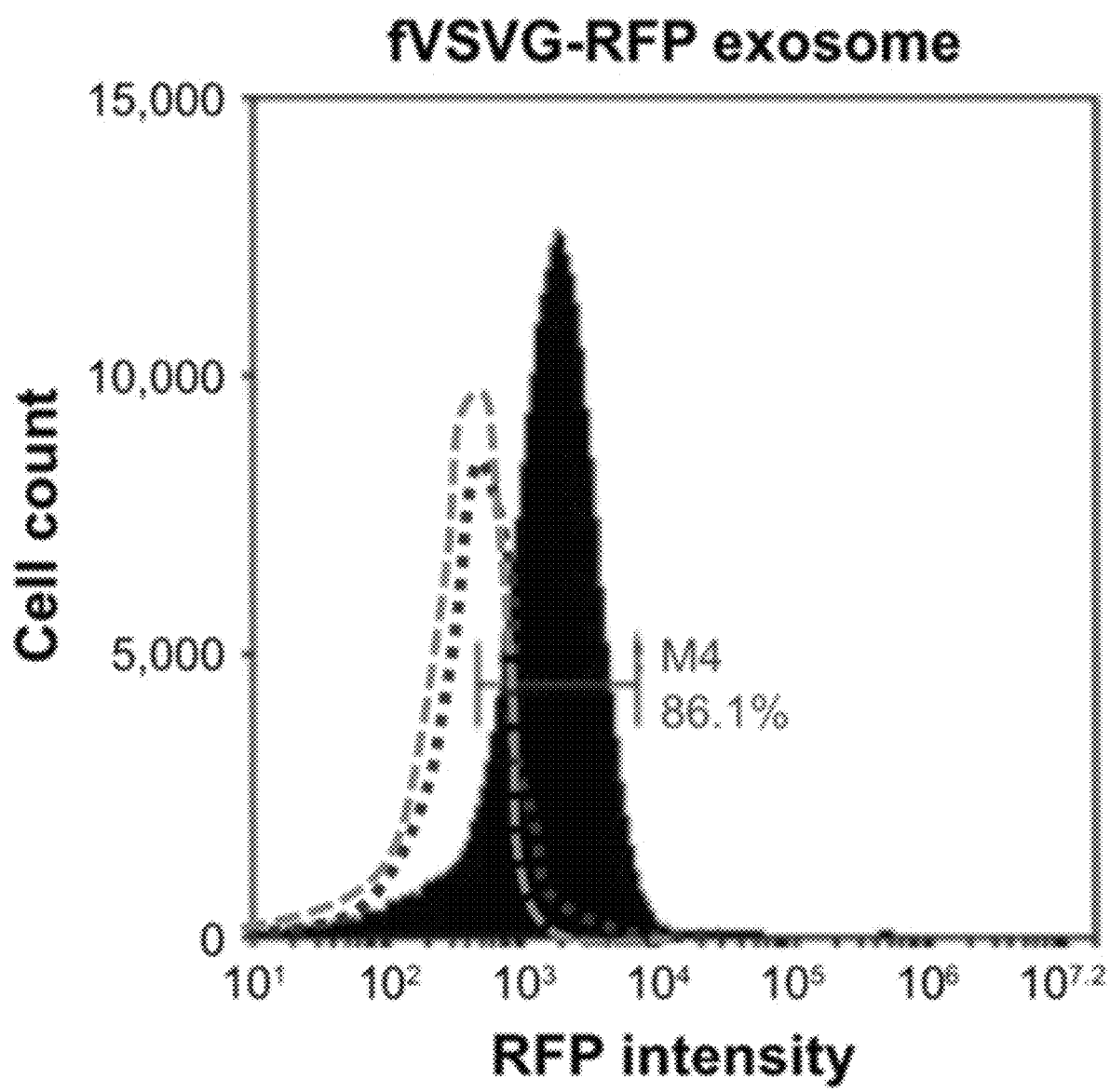
Figure 7D:
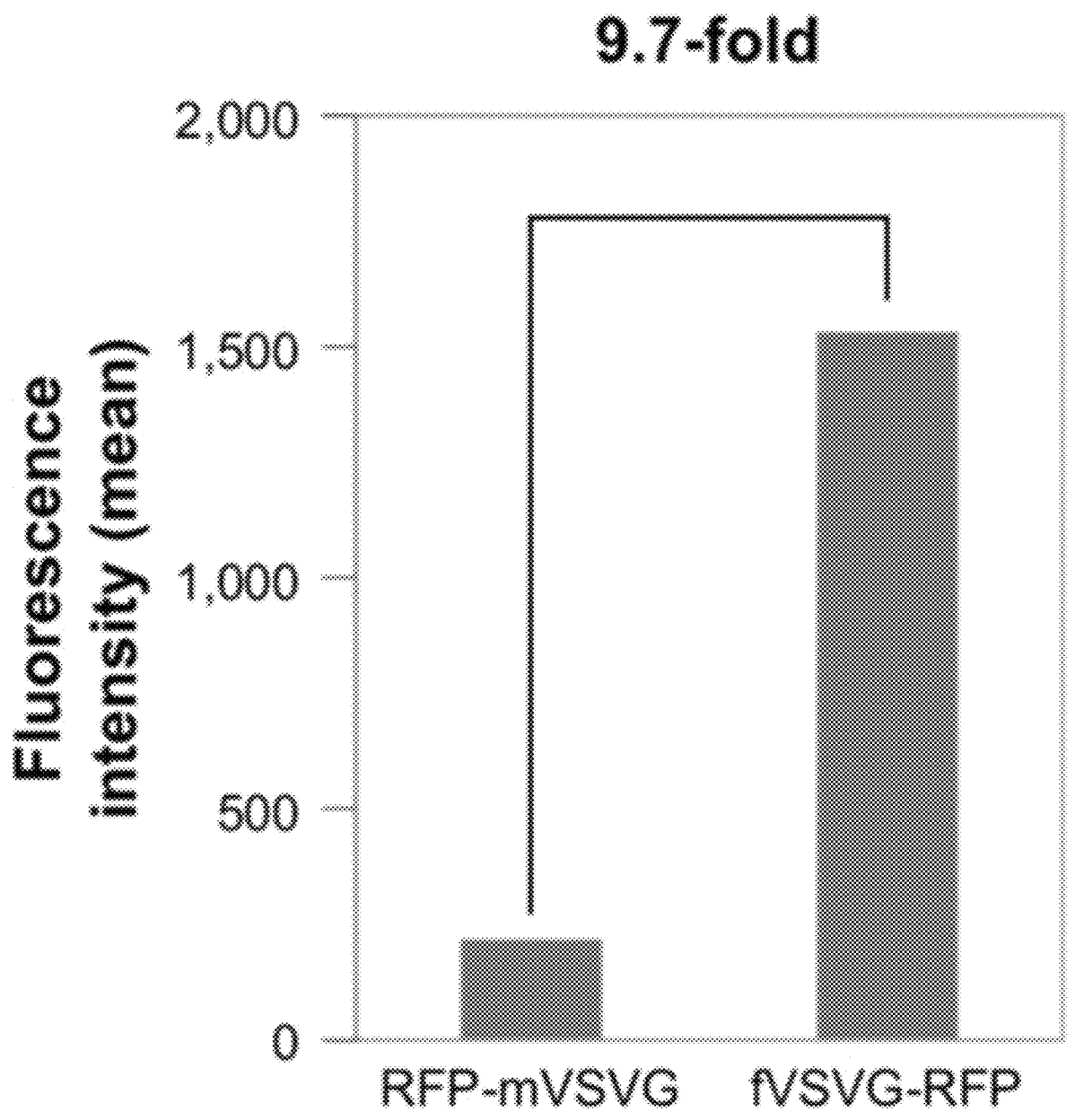

Next, we used fluorescence-activated cell-sorting analysis to quantify further the uptake of differentially pseudotyped exosomes by human cells. In these studies, we compared the uptake of fVSVG-RFP-versus RFP-mVSVG-pseudotyped exosomes in HEK293 cells after a 48-hour incubation. The plots in FIG. 7A and FIG. 7B show the population of cells emitting RFP fluorescence shifted slightly to higher numbers for exosome types A and B compared to the control (FIG. 7C). However, after subtracting the background fluorescence signal measured from the negative control group, we measured a 9.7-fold increase in exosome uptake for fVSVG-versus mVSVG-modified exosomes (FIG. 7D). Similar results were obtained for exosome uptake in U87 cells (FIG. S3A-C as shown in Appendix A in U.S. Provisional Patent Application 62/531,478 filed Jul. 12, 2017, which is incorporated herein by reference), while a more robust increase of 11.5-fold was recorded by pseudotyping with fVSVG versus mVSVG (FIG. S3D as shown in Appendix A in U.S. Provisional Patent Application 62/531,478 filed Jul. 12, 2017, which is incorporated herein by reference). Together, our results demonstrated that the uptake of exosomes by diverse cell types can be enhanced by producing VSVG-pseudotyped exosomes bearing the ectodomain in this process.

Wild-type full-length vesicular stomatitis virus glycoprotein VSVG (fVSVG) coding sequence and protein sequences, as well as fusion protein configuration, sequences, and domain annotation are described in U.S. Provisional Patent Application 62/531,478 filed Jul. 12, 2017, which is incorporated herein by reference.

What is claimed is:

1. An engineered exosome for the delivery of bioactive cargo, comprising:
an exosome defining an inner-vesicle space and an outer-vesicle space, wherein the exosome incorporates a vesicular stomatitis virus glycoprotein (VSVG) transmembrane anchoring scaffold onto the membrane of the exosome,
wherein the VSVG transmembrane anchoring scaffold has a C-terminal attachment site in the inner-vesicle space,
wherein the VSVG transmembrane anchoring scaffold has a N-terminal attachment in the outer-vesicle space,
wherein a first peptide is attached to the C-terminal attachment site of the VSVG transmembrane anchoring scaffold so that the first peptide is located in the inner-vesicle space,
wherein a second peptide is attached to the N-terminal attachment site of the VSVG transmembrane anchoring scaffold so that the second peptide is located in the outer-vesicle space.

2. The engineered exosome as set forth in claim 1, wherein the second peptide is attached to the second terminal attachment site of the VSVG transmembrane anchoring scaffold so that the second peptide is located in the inner-vesicle space, wherein a full length VSVG serves as the scaffold, and wherein the second terminal attachment site is the N-terminus of the VSVG.

3. The engineered exosome as set forth in claim 1, wherein the second peptide is attached to the second terminal attachment site of the VSVG transmembrane anchoring scaffold so that the second peptide is located in the outer-vesicle space, wherein a truncated VSVG serves as the scaffold, and wherein the second terminal attachment site is the N-terminus of the VSVG.

4. The engineered exosome as set forth in claim 1, wherein the first peptide is an imaging protein, a protein drug, a suicide protein, an enzyme for replacement therapy.

5. The engineered exosome as set forth in claim 1, wherein the second peptide is a 6xHis tag for detection and purification, an imaging protein, a viral antigen epitope, a cancer antigen epitope, a single chain antibody, or a protein drug.

6. The engineered exosome as set forth in claim 1, wherein the second peptide is an imaging protein, a viral antigen epitope, a cancer antigen epitope, a protein drug, a suicide gene, a receptor for active biomolecules, or a therapeutic protein for replacement therapy.

* * * * *